United States Patent
Andreiko et al.

(10) Patent No.: US 7,229,282 B2
(45) Date of Patent: Jun. 12, 2007

(54) PROVIDING CUSTOM ORTHODONTIC TREATMENT WITH APPLIANCE COMPONENTS FROM INVENTORY

(75) Inventors: Craig A. Andreiko, Alta Loma, CA (US); Daniel E. Even, Brea, CA (US)

(73) Assignee: Ormco Corporation, Orange, CA (US)

( * ) Notice: Subject to any disclaimer, the term of this patent is extended or adjusted under 35 U.S.C. 154(b) by 335 days.

(21) Appl. No.: 10/449,841

(22) Filed: May 30, 2003

(65) Prior Publication Data

US 2003/0224317 A1  Dec. 4, 2003

Related U.S. Application Data

(60) Provisional application No. 60/385,178, filed on May 31, 2002.

(51) Int. Cl.
*A61C 3/00* (2006.01)

(52) U.S. Cl. .................................................. 433/24

(58) Field of Classification Search .............. 433/24, 433/8, 215
See application file for complete search history.

(56) References Cited

U.S. PATENT DOCUMENTS

| 5,431,562 | A |   | 7/1995  | Andreiko et al. |
| 5,533,895 | A |   | 7/1996  | Andreiko et al. |
| 5,683,243 | A | * | 11/1997 | Andreiko et al. ............. 433/3 |
| 5,879,158 | A | * | 3/1999  | Doyle et al. ................. 433/24 |
| 6,089,868 | A |   | 7/2000  | Jordan et al. |
| 6,350,119 | B1 |  | 2/2002  | Jordan et al. |
| 6,532,299 | B1 | * | 3/2003 | Sachdeva et al. ........... 382/128 |
| 6,736,638 | B1 |  | 5/2004  | Sachdeva et al. |
| 2002/0028417 | A1 | | 3/2002 | Chapoulaud et al. |
| 2003/0163291 | A1 | * | 8/2003 | Jordan et al. .................. 703/1 |

FOREIGN PATENT DOCUMENTS

WO    WO 01/47405    7/2001

* cited by examiner

*Primary Examiner*—Melba Bumgarner
(74) *Attorney, Agent, or Firm*—Wood, Herron & Evans, L.L.P.

(57) ABSTRACT

Computer analysis is made of individual patient related data in order to select standard or pre-manufactured orthodontic appliances or appliance components (10) that are most likely to provide orthodontic treatment suitable for the individual patient. This analysis can be made by the software of a custom orthodontic appliance designing system, without actually manufacturing the custom appliance. Geometric parameters (21-24, 28, 29) of a custom designed appliance may be compared with corresponding parameters of alternative standard appliances or appliance components so that the closest standard component can be used. The custom appliance can be designed to accommodate the geometries of one or more appliance components. Where custom mounting instructions that modify otherwise standard installation of an appliance or component will render the standard component more compatible with a custom appliance design, such instructions are provided to the orthodontist along with the selection. The invention is most useful in selecting orthodontic brackets, or combinations of standard brackets and standard archwires.

5 Claims, 1 Drawing Sheet

PROVIDING CUSTOM ORTHODONTIC TREATMENT WITH APPLIANCE COMPONENTS FROM INVENTORY

This application claims priority to U.S. Provisional patent application Ser. No. 60/385,178, filed May 31, 2002.

FIELD OF THE INVENTION

This invention relates to orthodontic appliances and to the selection of components for such appliances to provide treatment suited for the particular patients.

BACKGROUND OF THE INVENTION

Orthodontic appliances are hardware devices that are attached to the teeth of patients, usually by orthodontic practitioners, to move malocclused teeth to better positions to improve the functionality of the teeth and the appearance of the patient. For decades, the most common orthodontic appliances have been formed of orthodontic brackets or bands that are secured to the patient's teeth and which are interconnected by an elastic archwire. Forces are applied by the archwire through the brackets and bands to the teeth to move them toward the desired positions.

The initial shape of the archwire for the treatment of a particular patient is generally prescribed by an orthodontist. Typically, the wire is bent during treatment so that the forces it applies affect the intended movements of the teeth. Intelligent selection of brackets and archwires, or other orthodontic appliance components, by the orthodontist can lead to more efficient treatment and require less manipulation of the appliance by the orthodontist during the course of treatment of the patient.

Systems and methods for providing custom orthodontic appliances are gaining acceptance. These systems and methods take into account individual patient anatomy in designing and manufacturing the custom appliances on a case-by-case basis. Often, custom appliance designs are based on calculated ideal occlusions or treatment plans by or with the aid of computers or computer programs. The computers determine tooth setups or post-treatment tooth positions based on digital data of the tooth shapes and other dental anatomy of the individual patients. The resulting custom appliances, when properly designed and made, can be installed on the teeth of a patient by an orthodontist, usually using custom jigs or other positioning devices or techniques that may be provided with the custom appliances to insure placement of the appliances at predetermined positions on the teeth of the patients so that the appliance functions in the way for which it was designed. Properly installed, such a custom appliances can move the teeth of patients in less time and with a minimum of post-installation manipulation by the orthodontic practitioner. Systems and methods for providing custom orthodontic appliances are described, for example, in U.S. Pat. No. 5,431,562 and in PCT Publication No. WO01/47405, both hereby expressly incorporated herein by reference.

The manufacturing of a custom orthodontic appliance may not always be available or might not always be desired, either because of the cost or because the orthodontist might require appliance components or a special prescription that the automated custom appliance manufacturing system might not be equipped to provide. In such cases, manual selection of appliance components is made by the orthodontist from available inventories of standard or otherwise pre-manufactured components, which the orthodontic practitioner assembles to form the appliance to treat the patient.

Selection of pre-manufactured appliance components by an orthodontist usually involves a consideration of the patient's individual anatomy, which can include skeletal and soft tissue anatomy as well as dental anatomy. This consideration leads to a prescribed treatment plan. Traditionally, such determination by the orthodontic practitioner of a treatment plan involves certain estimations, based on the judgment and experience of the practitioner, by manually applying professionally accepted criteria. The orthodontist then typically selects an appliance design that will achieve that treatment plan, which may include picking individual archwires and brackets from inventory or from a catalog that will form an appliance to carry out the prescribed treatment.

Such selection of appliance components is time consuming for the orthodontist. The manual techniques currently employed lack the capability for making the most accurate analysis of the patient's anatomy and the best selection of appliance components. Accordingly, a need exists for improving the selection of pre-manufactured appliance components and for better approximating the features of a custom orthodontic appliance most suitable for treating an orthodontic patient.

SUMMARY OF THE INVENTION

An objective of the present invention is to provide orthodontic appliance components that are well suited for carrying out a custom orthodontic treatment plan for an orthodontic patient.

A more particular objective of the invention is to facilitate the selection of pre-manufactured or standard orthodontic appliance components that will conform closely to the configuration of an orthodontic appliance that is custom to the anatomy of the patient.

Another objective of the invention is to reduce chair time for the orthodontist and treatment time for the patient by providing the features of custom orthodontic treatment designed in a way that serves the objectives of custom appliances, making their advantages available to a degree, at least, to patients at a proportionately lower cost.

A further objective of the present invention is to provide a system and method for orthodontic treatment that will facilitate the selection of standard or pre-manufactured orthodontic appliances utilizing highly accurate, and economical automated appliance selection techniques. Particular objectives of the invention include providing the orthodontic patients to be treated with pre-manufactured or standardized orthodontic appliance components with the precision and other benefits of orthodontic appliance design and providing such patients with the precision and other benefits of computer assisted determinations of the ideal positions of the teeth of such patients and the improved orthodontic treatment results.

According to the principles of the present invention, an orthodontic practitioner is provided with a service or with equipment or both to select those optimal orthodontic appliance components that closely carry out a custom orthodontic treatment plan. Certain systems and methods, according to the invention, evaluate appliance components according to parameters of an orthodontic appliance design or treatment plan that is customized for a particular patient. Based on the evaluation, components are selected from those of a predetermined plurality of geometries as those best suited for treatment of the patient. The evaluation and selection may be made, for example, by comparing component geometries of a custom appliance designed for the patient with the geometries of those of the plurality, making the selection of components according to best-fit criteria.

Systems and methods according to the invention may also vary the design of a custom orthodontic appliance for a patient in order to optimize the fit or matching of the custom appliance component geometries with those of the predetermined geometries. As such, the overall appliance is made up of the selected components that use combinations of standard or pre-manufactured appliance components that best approximate the optimum overall appliance or satisfy all of the relevant considerations and criteria for appliance component selection. Such criteria and considerations may include cost, component availability, aesthetics, anatomical considerations of the patient, or other criteria that might be imposed.

Systems and methods according to the invention may also provide an orthodontic practitioner with information on the installation of appliance components on the teeth of a patient in a way that best functions as a custom orthodontic appliance or best accomplishes a custom orthodontic treatment plan.

Various computerized custom appliance design systems that are used to calculate the custom appliances of various types, may be used to select standardized components from which an appliance may be assembled from pre-manufactured components, or components of predetermined geometries, from inventories or from shapes that can be efficiently manufactured to order. Such systems may be so used for this purpose rather than for the custom manufacture of an appliance or components of the appliance for the individual patient on a case-by-case basis. For example, portions of systems that design custom appliances in the forms of series of elastomeric positioners may be used to derive tooth finish positions for which components of bracket and archwire appliances, or appliances using other types of components, may be selected. In addition, other data analysis services may be used to process anatomical data for use in making orthodontic appliance or appliance component selections.

According to one embodiment of the invention, a virtual or physical impression of the anatomy of a patient is communicated to a programmed computer. A physical impression may, for example, be shipped to an orthodontic appliance lab where a stone cast is made of the patient's teeth and scanned to produce three-dimensional or other data for input into a computer for analysis. The computer may also be located at the orthodontic practitioner's office or clinic. A scan may be made directly from the anatomy of the patient, for example optically or by x-ray. The scanned data may be preprocessed or input directly into the computer. The computer may then analyze the data. An orthodontic practitioner may also use third party services that produce three-dimensional or other digital files of the dental anatomy of the patient for transmission to another facility for custom appliance design. A custom appliance design facility may typically design an occlusion or case set-up ideal for the patient, from which the design of a custom orthodontic appliance for the patient may be made that would move the patient's teeth to their ideal positions. Selection of an appliance or appliance components from available pre-manufactured items or from a discrete number of predetermined geometries or types may be made of those most suited to approximate the custom appliance or to otherwise move the patient's teeth to the ideal positions.

As an alternative or an addition to the inputting of anatomical data into the computer, treatment plan criteria may be articulated by the orthodontist, which the computer then analyzes. Such treatment plan criteria may include a prescription of orthodontic treatment that may specify, in part, final relative or individual tooth position or orientation geometry or may call for tooth extractions other properties of the desired positions of the patient's teeth or of the manner in which the teeth are to be treated.

Whatever data is analyzed by the computer, the computer may derive parameters or characteristics of a custom orthodontic appliance or of properties that may be embodied in an appliance of custom design or configured to implement a custom treatment plan. The derived information may then be compared with stored geometric or other physical data of available appliance components and a selection of components is made as a result of the comparison. The selected components may be those which, when assembled into an appliance and installed on the teeth of the patient whose data was processed, replicates an appliance of a derived custom appliance design or that produces the custom treatment plan.

The analysis of the data may also take into account the parameters of available appliance components and may conform the derived custom appliance to a configuration that most effectively uses standard or other available appliance components. Several iterations may be made. The final component selection may be one that exactly conforms to the design of a custom appliance or that conforms substantially to a custom design with minimum manual adaptation.

Where the selection of appliance components does not exactly conform to all of the criteria of a custom appliance or does not achieve all of the objectives of a custom treatment plan, the analysis may generate information for installation or modification of the appliance by the treating practitioner.

These and other objectives and advantages of the present invention are more readily apparent from the following detailed description.

DETAILED DESCRIPTION OF EMBODIMENTS OF THE INVENTION

Figure 1:
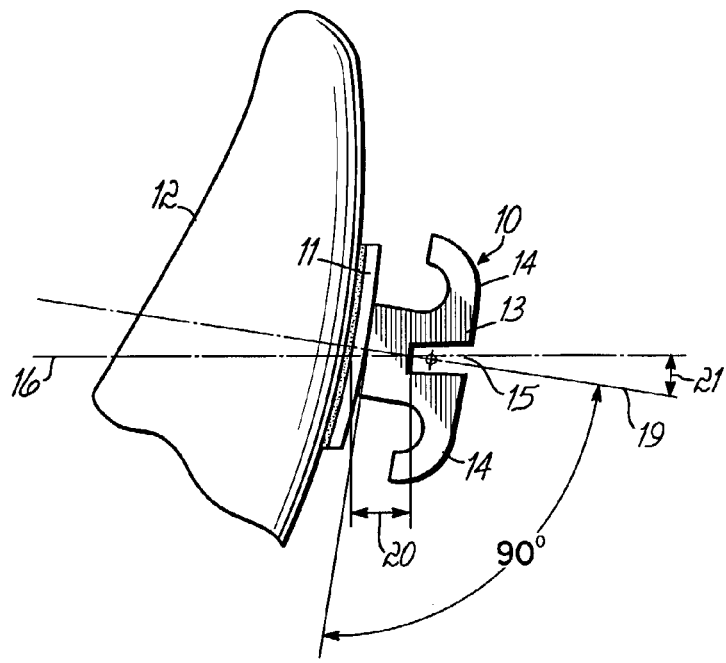
FIG. 1 is a diagram of a side view of a standard orthodontic bracket used to illustrate application of principles of the present invention, with one alternative group of geometric parameters marked thereon.

According to one embodiment of the invention, an orthodontist initially examines a patient for the purpose of diagnosing malocclusion of the patient's teeth and devising a treatment plan to correct the malocclusion. In doing so, the orthodontist may decide generally on the course of treatment and on the type of appliance to be used in the treatment. A decision may be made by the orthodontist and patient to proceed with treatment using standard appliance components. The appliance may, for example, be an orthodontic brace that includes upper and lower archwires to be supported on the respective upper and lower teeth of the patient by buccal tubes fixed to tooth-encircling bands secured to molars of the patient and by brackets bonded to the other teeth of the patient with dental adhesive.

Such braces have traditionally been assembled by the orthodontist from appliances or appliance components that are periodically stocked in inventory in the orthodontist's office. Brackets, buccal tubes and archwires, for example, have been manufactured in various standard sizes and shapes by orthodontic appliance manufacturers. The orthodontist periodically stocks the inventory by selecting and ordering them from catalogs and product bulletins of the manufacturers. Examples of such appliances and appliance components are described in U.S. Pat. No. 5,533,895 to Craig A. Andreiko et al. entitled Orthodontic Appliance and Group Standardized Brackets Therefor And Methods of Making, Assembling And Using Appliance to Straighten Teeth, in U.S. Pat. No. 5,474,448 to Craig A. Andreiko et al. entitled Low Profile Orthodontic Appliance and in U.S. Pat. No. 5,464,349 to Craig A. Andreiko et al. entitled Orthodontic Appliance Providing For Mesial Rotation Of Molars, each of which is hereby expressly incorporated herein by reference. Many other appliances and appliance components are available to orthodontists from different manufacturers.

Typically, the orthodontist studies the anatomy of the patient and considers the treatment plan to be prescribed. Then, the orthodontist selects standard brackets and other orthodontic appliance components from among the standard or pre-manufactured appliance components described above. The appliance components selected are those deemed most appropriate for the construction of an appliance in the form of a set of braces to be used to treat the patient in a manner most suited for the patient.

According to certain embodiments of the present invention, rather than the orthodontist completely performing the analysis and selection of appliance components, the orthodontist communicates details of the patient's anatomy to an orthodontic appliance facility or a processing facility, which analyzes the data and makes the selection for, or aids in the selection by, the orthodontist of appliance components. The communication may be in the form of data sent to the facility. The data may be sent in any of several ways, including but not limited to digital data, digitally transmitted, acquired from digital scans of the patient, from visually acquired pictures or x-rays, or physically transmitted in the form of a stone model or an impression.

In accordance with one preferred embodiment of the invention, physical impressions of the patient's dental arches are sent to the orthodontic appliance facility or data processing facility. The orthodontist may also make a stone model from the impression and transmit this to the facility instead of or in addition to the impression. A prescription and other information may also be sent by the orthodontist. The receiving facility may, if an impression is received, make a plaster cast or model from the impression. The facility may then scan the model or impression to produce three-dimensional data of the shapes of the patient's teeth, and may also produce data of the arrangement of the teeth in the patient's mouth prior to treatment.

This and other data of the patient may then be input to a computer by the orthodontic appliance or data processing facility operators, and software is run on the data which may, wholly automatically or interactively with an operator or technician, determine ideal positions of the patient's teeth to be achieved as a result of proposed treatment. This may result in a calculated occlusion or setup or other digitized model of the teeth in their post-treatment positions that may be further processed by, or sent to an appliance design facility, or returned to the orthodontist.

From the digitized model of the ideal tooth positions, the information is further processed at an appliance design facility to design a custom orthodontic appliance particularly suited for the treatment of the patient. The calculation may proceed in any of several ways, including calculating the geometry of a custom appliance without regard to the geometries of pre-manufactured components. The appliance design calculation results in calculated geometries for appliance components, including, for the more conventional type of appliance, geometries of brackets and archwires. These geometries are then compared with data of the pre-determined appliance component geometries to arrive at selections of components of those geometries for use in assembling the appliance for the patient.

The comparison may alternatively be achieved in the course of the calculation by inserting the geometries of one or more of the predetermined component geometries into the calculation and designing of the other components to best match the seeded values. Different geometries can be seeded and algorithms can be used to evaluate the geometry of the resulting appliance to optimize the overall appliance based on an optimal combination of component selections.

Examples of systems and methods for automatically designing custom orthodontic appliances are described in U.S. Pat. No. 5,431,562 and in PCT Publication No. WO01/47405, discussed above and incorporated by, reference herein, but other automated set-up software has been described or is available on the market, and may be suitable.

Figure 2:
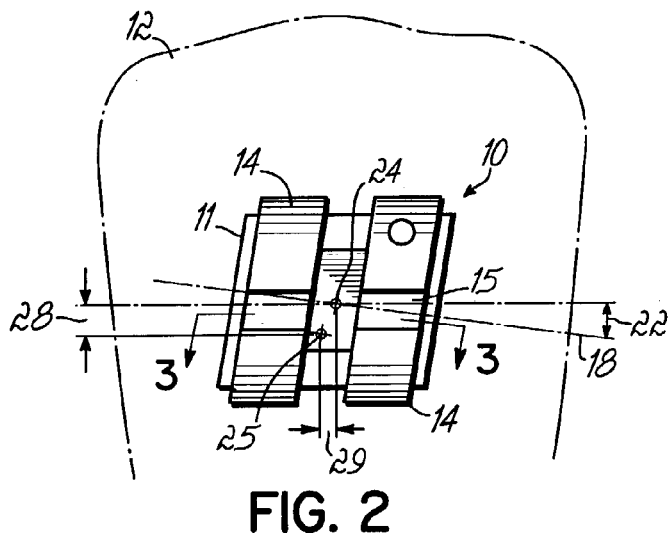
FIG. 2 is a front view diagram of the bracket of FIG. 1.
Figure 3:
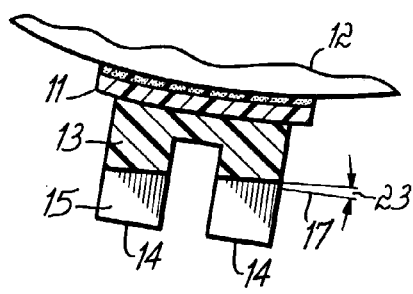
FIG. 3 is a top view diagram of the bracket of FIG. 1.

For example, software at the appliance facility may be used to calculate operative parameters of the components of a custom appliance, which may include, for example, the shape of an archwire or certain geometric characteristics of an orthodontic bracket, which are typically different for each tooth. A typical orthodontic bracket 10, for example, is illustrated in FIGS. 1–3. The bracket 10 includes a base or pad 11 that is bonded with adhesive to a tooth 12. Archwire support structure 13 is integrally formed with, or welded or otherwise fixed to, the pad 11. This support structure 13 is often formed of a pair of tie wings 14, having a rectangular archwire slot 15 formed therein in which an archwire, usually also of rectangular cross section, may be mounted and held with a ligature (not shown) that extends around the tips of the tie rings. The archwire will have a curvature and lie in a plane 16. Comparable appliances to the bracket 10 include buccal tubes that are often used on one of the molars on each side of each arch, in which the base 11 is in the form of a tooth-encircling band and the support structure is in the form of an enclosed tube in which the tips of an archwire are inserted.

Typical parameters that describe an orthodontic appliance are embodied in the bracket 10, and may differ from patient to patient when a custom orthodontic appliance is designed. One of these parameters is an in-out dimension 20, which may be defined as a distance to an archwire slot 15 from a point on the bracket base 11 that bonds to the tooth 12 in the plane of the archwire 16. Another parameter is the torque or slot inclination angle 21, which is the angle of the archwire plane to a line 19 normal to the surface of the tooth 12 where the base 11 is mounted. A further parameter is the tip angle 22, which is the angle between the archwire and a line 18 normal to the axis of the tooth in the mesial-distal direction. Still another parameter is the rotation angle 23, which is the angle between the archwire and a line 17 normal to a plane bisecting the tooth in the mesial distal direction and in which plane the tooth axis lies. These appliance parameters are more fully defined in U.S. Pat. Nos. 5,431,562 and 5,533,895, hereby expressly incorporated herein by reference, and other patents that have been referred to elsewhere herein.

In addition to the parameters discussed above, appliance placement information that defines the placement of an appliance component, such as a bracket 10, is characteristic of a ideal custom appliance. These may be defined to include horizontal and vertical offsets 28, 29 from a point 24 at the center of the appliance base 11 to the center 25 of the face of the tooth 12 at which a standard appliance of the type 10 would customarily be mounted on the tooth 12. The position at which the bracket base is to be mounted to the tooth is a parameter calculated by most custom appliance design software. Since the brackets being selected are standard brackets that will be placed on the teeth by an orthodontist using conventional manual techniques, the bracket mounting locations on the teeth at which the brackets are customarily placed is taken as given, at least initially in the appliance design calculations. Manual placement positions and techniques are described in the patents discussed above and in U.S. Pat. Nos. 5,993,206 and 6,358,044 by Craig A. Andreiko entitled Visual Positioning Orthodontic Appliance and Method, hereby expressly incorporated by reference herein.

According to one method of the invention, a custom orthodontic appliance design is calculated by a computer from data scanned from a model of the patient's teeth and other data of the patient's anatomy and the custom treatment plan or prescription. The appliance design calculation typically, in the automated custom appliance systems referred to above at least, is based on a calculation of custom finish positions of the patient's teeth, often referred to as a custom set-up. The appliance is designed so that the archwire is supported in a stress-free state in brackets mounted to the patient's teeth when the teeth arrive at the finish positions of the calculated set-up.

The calculation may assume that orthodontic brackets will be placed on these teeth in a conventional manner by the orthodontist, so that the custom appliance design may be based on such bracket placement positions. Then, with a custom archwire shape selected, the custom archwire geometry may be compared with the geometries of standard archwire geometries and archwires for the appliance are thereby automatically selected.

The calculated archwire shape and the positions of the teeth in the calculated set-up are used to calculate the torque, tip, rotation and in-out parameters of the slots of brackets mounted in the assumed mounting positions. Alternatively, rather than use the calculated archwire shape, the shape of the standard archwire that was selected to best approximate the calculated custom archwire shape may be used, which will reduce cumulative error. The resulting bracket parameters are then compared to the parameters of available standard brackets and the standard brackets that are the closest fit to calculated parameters are selected.

Alternatively, rather than select each bracket of the appliance that is the best fit, the parameters of the selected brackets may individually be substituted for those of the corresponding calculated parameters of the custom bracket, and the appliance redesigned so that the custom appliance uses the parameters of the standard bracket exactly. Then, different combinations of standard bracket parameters may be substituted and the custom appliance redesigned then evaluated against some criteria. In this iterative manner, an appliance that best uses the most standard brackets with a minimum of difference between the standard and calculated parameters can be selected. This method may also be used to adjust the appliance exactly to all but one or a few of the standard appliance components, leaving only the one or few to be customized to render the appliance fully custom.

Further, where the calculated parameters of one or more particular custom brackets cannot be closely matched by any of the available standard brackets, a custom recommendation can be provided with the bracket selections to the orthodontist to aid the orthodontist in modifying the placement or mounting of one or more brackets to compensate for whatever error exists between the selected standard bracket and the custom bracket it is intended to simulate. For example, a recommendation might be made that the orthodontist mount a bracket a certain small distance mesial of the standard mounting position to produce an adjustment to the slot rotation, or that the bracket be tipped or mounted higher or lower in relation to the tip of the tooth to produce a tip or torque adjustment.

Typically, tooth anatomy is sufficiently consistent from patient to patient that no comparison with standard brackets of different base configurations is needed in order to fit brackets to the teeth. Usually, due to the relatively small bracket base sizes, the relatively smoothly curved facial surfaces of the teeth can be accommodated by a single base curvature for each given tooth. An exception to this is for the case of banded appliance bases, which are often used to mount buccal tubes to molars, that may require different sizes to fit molars of different sizes. Therefore, except for buccal tubes on molars, no selection need be made based on a comparison of standard bracket parameters to tooth size or particular tooth dimensions. The selection may in most cases be based only on a comparison of standard appliance geometric parameters with those of a corresponding component of a custom appliance.

While it is preferred that: the selection be based on the scanning of data, the generation of three-dimensional images of each of the patient's teeth, the calculation of a custom set-up, and the design of a custom orthodontic appliance therefrom, benefits of the invention can be realized in other ways. Interpretive information from the orthodontist based on observations of the patient's anatomy or information regarding a prescribed treatment can be the basis for computer analysis from which standard appliance selection can be made to assist the orthodontist in carrying out an effective and efficient treatment plan. The interpretation of x-ray or photographic data or measurement data can also lead to an intelligent selection of standard appliance components that will more closely approximate an ideal custom appliance than might otherwise be the case.

The method and system can be used to generate with a computer, from the various types of patient specific information provided, the physical characteristics of custom appliance components for the patient, such as customized archwires, customized brackets, etc., and to present the orthodontist with the customized component characteristics or component selection, or with a representation of the set-up or final tooth positions that such components would produce, providing the orthodontist with the opportunity to specify modifications to the appliance, tooth positions or treatment, or to provide further input data for further analysis and selection.

The invention may also be used to specify appliances that combine standard brackets with custom archwires, or standard archwires with custom brackets, or standard brackets with custom brackets, or for other combinations of standard and custom appliance components. In this way, the customizing manufacturing operations can be confined to one or less than all of the appliance components, while still producing an appliance that is at least partially custom and functions as well as, or approaches the functions of, a custom appliance, at least to a degree that is superior to a traditionally assembled appliance made up of standard components.

For purposes of the claims, the term "appliance" is used to refer to either that which makes up the entire hardware to treat an orthodontic patient or to one or more individual components of such hardware.

The invention has been described in the context of exemplary embodiments. Those skilled in the art will appreciate that additions, deletions and modifications to the features described herein may be made without departing from the principles of the present invention.

The invention claimed is:

1. A method of selecting orthodontic appliances comprising:
   providing digital information that is a representation of individual dental anatomy of a patient;
   analyzing the digital information with a computer to derive geometric parameters of a custom orthodontic appliance;
   comparing the derived geometric parameters with corresponding parameters of a plurality of alternative pre-manufactured orthodontic appliances and selecting one of the plurality based on the comparison;
   wherein the providing of the digital information includes any one of the following:
      a) forming a physical impression of a patient's teeth at a situs of an orthodontic practitioner, transporting the impression to an orthodontic appliance facility, forming at the orthodontic appliance facility a solid model of the patient's teeth from the impression, scanning the model to produce three-dimensional digital information of the shape of the patient's teeth;
      b) digitizing skeletal information of the patient;
      c) digitizing soft tissue information of the patient;
      d) digitizing dental information of the patient other than as set forth in a); or
      e) digitizing x-rays of skeletal, soft tissue or dental information of the patient; and
   wherein the analyzing of the digital information includes designing with a computer the orthodontic appliance that includes a custom orthodontic archwire and a set of custom orthodontic brackets to be bonded to each of a plurality of the patient's teeth to support the archwire to achieve an arrangement of the patient's teeth by orthodontic treatment.

2. The method of claim 1 wherein the geometric parameters include slot in-out, slot torque, slot tip and slot rotation of each of the orthodontic brackets of the set.

3. The method of claim 2 further comprising providing the selected appliance to an orthodontic practitioner for treatment of the patient.

4. The method of claim 1 further comprising providing the selected appliance to an orthodontic practitioner for treatment of the patient.

5. A method of selecting orthodontic brackets comprising:
   forming a physical impression of a patient's teeth at a situs of an orthodontic practitioner;
   transporting the impression to an orthodontic appliance facility;
   at the orthodontic appliance facility, scanning the impression or a model made therefrom to produce three-dimensional digital information of the shape of the patient's teeth;
   analyzing the three-dimensional digital information with a computer to derive an arrangement of the patient's teeth to be achieved by orthodontic treatment;
   designing with a computer a custom orthodontic appliance that includes a custom orthodontic archwire and a set of custom orthodontic brackets to be bonded to each of a plurality of the patient's teeth to support the archwire to achieve the derived arrangement by the orthodontic treatment;
   comparing geometric parameters that include slot in-out, slot torque, slot tip and slot rotation of each of the custom orthodontic brackets of the set with corresponding parameters of each of a plurality of standard or pre-manufacture red orthodontic brackets for a tooth and selecting one of the plurality of standard or pre-manufactured brackets based on the comparison; and
   providing the selected brackets or information on the selection to an orthodontic practitioner for treatment of the patient.

* * * * *